United States Patent
von Bünau et al.

(10) Patent No.: US 10,194,797 B2
(45) Date of Patent: Feb. 5, 2019

(54) METHOD FOR SELECTING AN INTRAOCULAR LENS TO BE IMPLANTED INTO AN EYE

(71) Applicant: Carl Zeiss Meditec AG, Jena (DE)

(72) Inventors: Rudolf Murai von Bünau, Jena (DE); Tobias Bühren, Magdala (DE)

(73) Assignee: Carl Zeiss Meditec AG, Jena (DE)

( * ) Notice: Subject to any disclaimer, the term of this patent is extended or adjusted under 35 U.S.C. 154(b) by 36 days.

(21) Appl. No.: 15/167,688

(22) Filed: May 27, 2016

(65) Prior Publication Data

US 2016/0345825 A1 Dec. 1, 2016

(30) Foreign Application Priority Data

May 29, 2015 (DE) .......................... 10 2015 209 886

(51) Int. Cl.
*A61B 3/10* (2006.01)
*A61B 3/00* (2006.01)
*A61F 2/16* (2006.01)

(52) U.S. Cl.
CPC .......... *A61B 3/1005* (2013.01); *A61B 3/0025* (2013.01); *A61F 2/16* (2013.01)

(58) Field of Classification Search
CPC ................ A61B 3/0025; A61B 3/1005; A61B 2090/061; A61B 3/10; A61B 3/102; A61B 3/103; A61B 3/107; A61B 3/112; A61B 3/1173; A61B 3/12; A61B 90/06; A61F 2/16; A61F 2/1613; A61F 2/1637
USPC ........ 351/200, 205, 206, 209–211, 221, 222, 351/243–246
See application file for complete search history.

(56) References Cited

U.S. PATENT DOCUMENTS

| 10,123,687 B2 | 11/2018 | Bühren et al. |
| 2014/0192317 A1* | 7/2014 | Buhren .................... A61B 3/10 351/205 |
| 2014/0379268 A1 | 12/2014 | Becker et al. |

(Continued)

FOREIGN PATENT DOCUMENTS

DE  10 2011 075 0149 A1  12/2011
DE  10 2013 020 706 A1   6/2015

OTHER PUBLICATIONS

Einighammer et al., "Customized aspheric intraocular lenses calculated with real ray tracing" J Cataract Refract Surg, vol. 35, Nov. 2009, pp. 1984-1994.

(Continued)

*Primary Examiner* — Brandi Thomas
(74) *Attorney, Agent, or Firm* — Patterson Thuente Pedersen, P.A.

(57) ABSTRACT

A method for selecting an intraocular lens (IOL) to be implanted into an eye, in which the selection is based on a non-paraxial approach. In a ray tracing method for selecting an intraocular lens to be implanted into an eye with a simplified, centered optical system, in addition to the pre-operatively measured biometric values, the effective lens position of the corresponding eye and the optical transfer function of the IOLs are used, which are calculated for a standardized distance behind the equatorial plane of the IOL. The method may be used to select an intraocular lens to be implanted into an eye and is equally suitable for spherical, aspherical, toric and multifocal IOLs.

12 Claims, 1 Drawing Sheet

(56) References Cited

U.S. PATENT DOCUMENTS

2015/0250583 A1* 9/2015 Rosen ..................... A61B 3/14
623/6.23

OTHER PUBLICATIONS

Preussner et al., "Intraocular lens calculation accuracy limits in normal eyes", J. Cataract Refract Surg, vol. 34, May 2008, pp. 802-808.
Preussner et al., "Ray tracing for intraocular lens calculation", J. Cataract Refract Surg, vol. 28, Aug. 2002, pp. 1412-1419.
Thibos et al., "Accuracy and Precision of Objective Refractive from WAvefront Aberrations", Journal of Vision, 2004, pp. 1-8.
German Search Report (German Language and English Translation), dated Dec. 18, 2015, 20 pages.

* cited by examiner

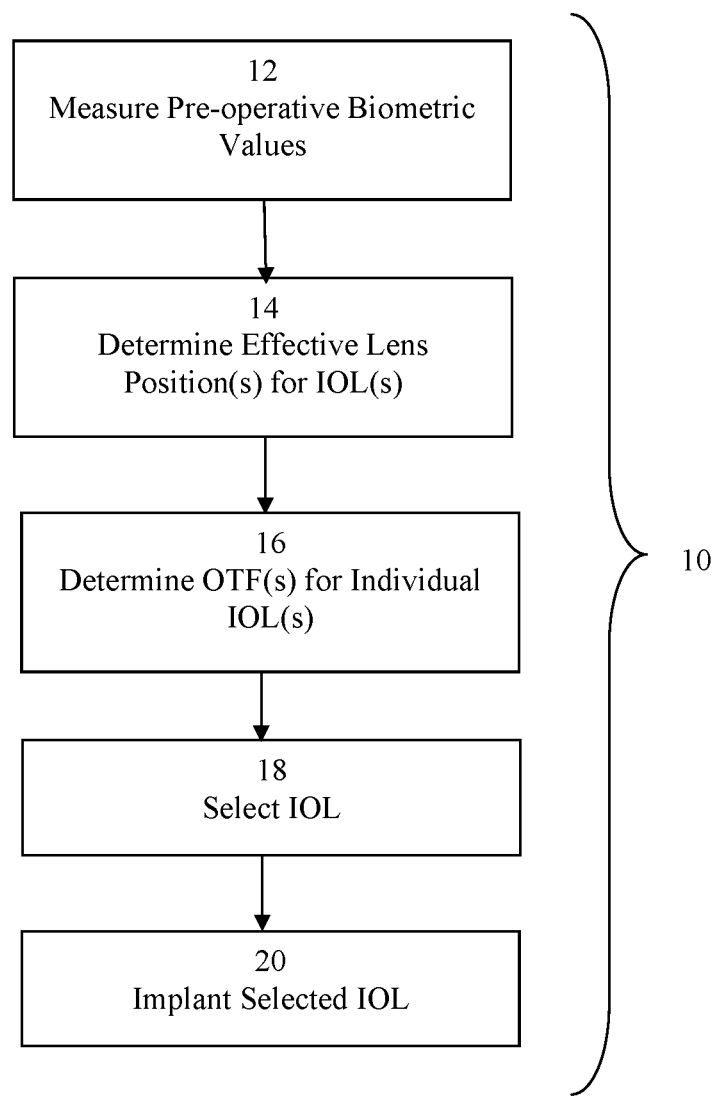

METHOD FOR SELECTING AN INTRAOCULAR LENS TO BE IMPLANTED INTO AN EYE

RELATED APPLICATIONS

The present application claims priority to German Application No. 102015209886.9, filed May 29, 2015, said application being incorporated herein in its entirety by reference.

TECHNICAL FIELD

The present invention relates to a method for selecting an intraocular lens (IOL) to be implanted into an eye, in which the selection is based on a non-paraxial approach.

BACKGROUND

According to the known prior art, IOLs are selected and adapted on the basis of measured and/or estimated variables, with only individual parameters being considered in the form of individual measured values or as a mean value over defined patient groups.

The selection or adaptation of the optimal intraocular lens (IOL) is done exclusively according to their characteristics, such as type, refractive power, asphericity and multifocality.

The selection of the appropriate intraocular lens (IOL) for a patient is the responsibility of the cataract surgeon. In making this selection, the surgeon must consider many factors. For one, the appropriate method for calculating the IOL dioptric power must be selected as a function of the individual biometric parameters of the eye. To this end, for unusually long, normal or unusually short eyes, various more or less appropriate formulas can generally be used for the calculation. In the simplest of cases, their input parameters are based on keratometry and the axial length of the eye, the formulas usually also containing, due to their simplified modeling assumptions, an empirically determined correction factor, such as the so-called A-constant, for example.

The method of calculation that is currently most widely used are so-called IOL formulas, for example according to Holladay, Hoffer, Binkhorst, Colenbrander, Shammas, or SRK. According to those, the refraction D (output/assessment parameter) of the patient after inserting the IOL is calculated as follows:

$$D = D_{IOL} - f(K, AL, VKT, A) \quad (1)$$

where
  f( ) is a standard, known IOL formula and
  $D_{IOL}$ is the refractive power of the IOL,
  K is the measured keratometry value,
  AL is the measured axial length of the eye,
  VKT is the measured anterior chamber depth, and
  A is an IOL-type-dependent constant constituting the input variables.

The constant A in the formulas is determined empirically over a patient cohort in order to adapt the expression values to the actual resulting optimal refraction values. However, the adaptation only ensures that the mean of the refraction values matches with the formula over the test cohort.

These methods of calculation are based on a paraxial approach, that is, on first-order optics. In this simplification of geometrical optics, only those light beams are observed that do not form an angle with the optical axis and are at short distances from it, thus resulting in linear formulas for calculating the light beams passing through the system. Besides chromatic aberration, paraxial beams cannot cause imaging errors; that is, such errors can be ruled out when using monochromatic light itself.

SUMMARY

The current calculation formulas based on the paraxial approach operate on a series of simple assumptions:
  The higher-order asphericity and aberrations of the cornea are not taken into consideration,
  The posterior corneal curvature is derived from the anterior curvature as a so-called Gullstrand ratio, and
  The refractive power of the IOL is constant over its entire power range.

These simplifications and assumptions can have a disadvantageous effect, particularly in the selection of aspherical, multifocal and toric IOLs, and can lead to a non-optimal or even faulty selection of the IOL to be implanted.

An alternative method for improving the accuracy of the selection of an IOL to be implanted in an eye is so-called ray tracing. As the term indicates, ray tracing is a method for mapping the path of light rays.

As is known, we see things in our environment only because they are irradiated by a light source and reflect these light rays, a portion of which ends up reaching our eyes. The ray tracing method simulates this elementary natural phenomenon. If the optical system, that is, the individual human eye with all of its optical elements, is known, then ray tracing can be used to calculate a "real" image forming on the retina. The method is thus based on a detailed eye model that uses the corneal topography of the eye. In this method, no general correction factors (A-constants) are used, but certain assumptions regarding what the effective (postoperative) lens positions (ELP) are required. This method is suitable for eyes with an extremely wide range of biometric parameters, such as: long, normal, short, post-LASIK.

The IOL dioptric power and the residual refraction are then calculated with the aid of ray tracing. In order to achieve a good correlation with the subjective acuteness of vision, i.e., a result that is comparable to the patient's perception, various selection criteria or metrics can be used for the calculation.

While Von P.-R. Preussner et al. [1] performs a comparison between the use of ray tracing methods and other IOL formulas, a calculation model is explored more closely in [2] that is based on a ray tracing method. Here, based on the individual measured values and estimated variables, such as, in particular, the position of the IOL in the eye, an eye model is developed that generally has several, optically effective surfaces, and this is "calculated out" for one or more beams using optical design methods. The imaging quality on the retina/fovea is calculated as an assessment value. With a commensurately precise determination of the input variables, systematic errors can thus be prevented to the greatest possible extent. Statistical errors such as those resulting from a lack of reproducibility of the measurements or from variability in the wound healing process, for example, are not taken into account here, however.

Another method for calculating the exact geometry of customer-specific IOLs for pseudophakic eyes that is based on ray tracing is described by J. Einighammer et al. in [3]. Here, an individual calculation model is constructed on the basis of measurements. In the optimization process, into which the geometry of the customer-specific IOL is integrated, the minimum of the wavefront error is searched for by means of so-called "real ray tracing."

It was studied by L. N. Thibos in [4] to what extent the use of different metrics, such as pupil-plane or image-plane metrics, for example, impacts accuracy and precision in anticipating the results of wavefront aberrations. It turned out that, on the one hand, there are indeed differences in the precision of the prediction, but that, on the other hand, the accuracy of all of the methods can be improved by correcting the systematic distortion.

In addition to the IOL dioptric power, certain characteristics such as asphericity or toricity of the cornea can provide indications for certain IOLs. In the case of so-called premium IOLs, the surgeon, after clarification with the patient, can opt for IOLs, such as multifocal lenses, for example, that perform special visual tasks. Such IOLs are intended to enable the patient to perform visual tasks at a distance and at close range, even without additional visual aids. How the IOLs used in individual eyes ultimately meets the requirements placed on them depends on many factors, such as the optics of the cornea, the implantation technique, the optical or mechanical design of the IOL, the pathologies of the eye, etc.

The fundamental problem with ray tracing is that IOL manufacturers are generally not willing to disclose the design data for particular IOLs necessary for a ray tracing calculation. This is especially true of innovative lens types, such as aspherical, multifocal and toric IOLs, for example, for which a ray tracing approach would be especially highly beneficial for those on the other side.

REFERENCES

[1] Preussner, P. R. et al., "Intraocular lens calculation accuracy limits in normal eyes," J CATARACT REFRACT SURG, Vol. 34, May 2008;
[2] Preussner, P. R. et al., "Ray tracing for intraocular lens calculation," J CATARACT REFRACT SURG VOL 28, August 2002;
[3] Einighammer, J. et al., "Customized aspheric intraocular lenses calculated with real ray tracing," J CATARACT REFRACT SURG, Vol. 35, November 2009;
[4] Thibos, L. N., et al., "Accuracy and precision of objective refraction from wavefront aberrations," Journal of Vision (2004) 4, 329-351.

Each of these references is hereby fully incorporated herein by reference in its entirety.

It is the object of the present invention to use data for IOLs that are suitable and sufficient for ray tracing, but where the data are insufficient for a reconstruction of the design of the IOLs. This applies particularly to design data such as curvatures, asphericities, center thickness and refractive index, for example. In this way, the selection of the IOL to be implanted is to be simplified and the result of the refractive intervention on the eye improved.

This object is achieved with the inventive method for selecting an intraocular lens (IOL) to be implanted into an eye with the aid of a ray tracing method that is based on a simplified, centered optical system in that preoperatively measured biometric values and the effective lens position of the corresponding eye and the optical transfer function of the IOLs are used for the ray tracing method that are calculated for a standardized distance behind the equatorial plane of the IOL.

According to the invention, the object is achieved by the features of the independent claims. Preferred developments and embodiments are the subject matter of the dependent claims.

The proposed method based on a ray tracing method is used to select an intraocular lens to be implanted into an eye and is equally suitable for spherical, aspherical, toric and multifocal IOLs.

The invention is described below in further detail on the basis of exemplary embodiments.

BRIEF DESCRIPTION OF THE DRAWINGS

Subject matter hereof may be more completely understood in consideration of the following detailed description of various embodiments in connection with the accompanying figures, in which:

FIG. 1 is a flowchart of an exemplary process according to an embodiment of the invention.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

The inventive method involves a ray tracing method for selecting an intraocular lens to be implanted into an eye with a simplified, centered optical system. In addition to the preoperatively measured biometric values, the effective lens position of the corresponding eye and the optical transfer function of the IOLs are used, which are calculated for a standardized distance behind the equatorial plane of the IOL An optical transfer function (OTF) describes the imaging and reproduction quality of each individual IOL. It represents a quality function for the image-forming characteristics of an optical system—in this case, of the IOL. On the one hand, it can be calculated from the geometric aberrations and the aperture delineating the pupil as well as from the design data for various parameters and, on the other hand, determined with the aid of different methods of measurement.

In an exemplary process 10 as diagrammed in FIG. 1, pre-operative biometric values are measured in a first step 12. According to embodiments of the invention, the biometric values for axial length, topography and corneal thickness, and preferably also the curvature of the rear of the cornea, are used for a ray tracing method. In a second step 14, an effective lens position is calculated. Then, at 16, OTFs are calculated for the IOLs.

The OTF is a complex function whose quantity is the modulation transfer function (MTF) and whose argument is the phase transfer function (PTF) of luminance or illuminance distributions of different period length. The ratio of the modulation in the image to that in the object is called the modulation transfer function (MTF). However, the OTF can also be regarded as a Fourier transform of the intensity distribution of a dot image.

The optical transfer function (OTF) is calculated for a standardized (known) distance behind the equatorial plane of the IOL. According to embodiments of the invention, this distance lies in the range from 5 to 10 mm behind the defined equatorial plane of the IOL.

For the ray tracing method, besides the optical transfer function of the IOLs in question, the preoperatively measured biometric values and the effective lens position are used. To this end, it is necessary for the optical transfer function of the IOLs to be calculated for a (known) standardized distance behind the equatorial plane of the IOL.

It is especially advantageous if, instead of the effective lens position, the predicted actual lens position is used for the ray tracing method. Solutions have been proposed for this in the known prior art by Norrby, Olsen and Bissmann.

If the preoperatively measured biometric values, the effective or actual lens position of the corresponding eye and the optical transfer function of the usable IOLs are known, the intraocular lens to be implanted in the eye can be selected using a ray tracing method at step 18. And, finally, the IOL is implanted at step 20.

The ray tracing can be done both by means of ray tracing from infinity and from a finite object distance. The beams are also a measure for the predicted wavefront error for the combination of the corresponding eye and the IOL to be selected.

According to a simplified variant of the method according to the invention, instead of the optical transfer function of the IOLs, data may be used for the ray tracing method that contain sets of input and output beams as follows:

$$\{h_i; \tan(\varphi_i)\}m \ \{h_i; \tan(\varphi_i')\}m$$

where $h_i$ refers to the height (distance) of the beams from the optical axis, $\tan(\varphi_i)$ refers to the angle between the beams and the optical axis, i refers to the number of beams on a semi-meridian, and m refers to the number of image distances from the reference plane, the data being based on a (known) standardized refractive index nV for the vitreous body of the eye and on the assumption that the reference plane of the equatorial plane of the IOL or of the insertion plane corresponds to the haptics.

According to a first advantageous embodiment, elevations between 0 and 5 mm are considered, the number of beams on a semi-meridian being i=5, preferably 1=10, and especially preferably i>15.

According to a second advantageous embodiment, image distances between 17 and 23 mm are considered, the number of image distances being m=5 and especially preferably m>10.

According to the invention, at least one, but preferably several such datasets are used for the ray tracing method in the case of spherical and aspherical IOLs.

In contrast, in the case of toric IOLs, at least two, but preferably several such datasets are necessary for the ray tracing method, and datasets of the two main meridians, i.e., of the steepest and flattest meridian, must be included.

Advantageously, image distances that are not available can be completed through interpolation.

With the inventive solution, a method for selecting an intraocular lens to be implanted into an eye is made available which is based on a ray tracing method with a simplified, centered optical system. The preoperatively measured biometric values, the effective lens position of the corresponding eye, and the optical transfer functions of the IOLs, which are calculated for a standardized distance behind the equatorial plane of the IOL, are used for the ray tracing method.

The proposed method enables both a simplified selection of the IOL to be implanted and an improved result of the refractive intervention.

The OTF determined for each IOL is suitable and sufficient for ray tracing, but due to the complexity of the OTF, the design data of the IOL design cannot be reconstructed.

It should be arithmetically impossible to reconstruct the design data from the IOL consisting of two refractive surfaces, even if the refractive index of the material and the center thickness of the IOL are known, since an inherent ambiguity remains.

It is therefore assumed that the manufacturers of IOLs will be willing to make the corresponding OTF for each of their IOLs available in a standardized format.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method for selecting an intraocular lens to be implanted into an eye with the aid of a ray tracing method, based on a simplified, centered optical system, wherein preoperatively measured biometric values, effective or actual lens position of the eye, and data is used for the ray tracing method that contain sets of input and output beams as follows:

$$\{h_i; \tan(\varphi_i)\}m\{h_i; \tan(\varphi_i')\}m$$

where $h_i$ refers to the height (distance) of the beams from an optical axis, $\tan(\varphi_i)$ refers to the angle between the beams and the optical axis, I refers to a number of beams on a semi-meridian, and m refers to a number of image distances from a reference plane, the data being based on a (known) standardized refractive index nV for a vitreous body of the eye and on an assumption that the reference plane of an equatorial plane of the intraocular lens or of an insertion plane corresponds to haptics of the intraocular lens, calculated for a standardized distance behind the equatorial plane of the intraocular lens.

2. The method of claim 1, wherein elevations between 0 and 5 mm are considered, the number of beams on a semi-meridian being i=5.

3. The method of claim 1, wherein image distances between 17 and 23 mm are considered, the number of image distances being m=5.

4. The method of claim 1, wherein at least one, dataset is used for the ray tracing method in the case of spherical and aspherical IOLs.

5. The method of claim 1, wherein in the case of toric IOLs, at least two datasets are used for the ray tracing method, it being necessary for datasets of both main meridians to be included.

6. The method of claim 1, wherein the image distances not made available are completed by interpolation.

7. The method of claim 1, wherein elevations between 0 and 5 mm are considered, the number of beams on a semi-meridian being i=10.

8. The method of claim 1, wherein elevations between 0 and 5 mm are considered, the number of beams on a semi-meridian being i>15.

9. The method of claim 1, wherein image distances between 17 and 23 mm are considered, the number of image distances being M>10.

10. The method of claim 4, wherein several datasets are used for the ray tracing method in the case of spherical and aspherical IOLs.

11. The method of claim 1, wherein in a case of tonic IDLs, several datasets are used for the ray tracing method, it being necessary for datasets of both main meridians to be included.

12. The method of claim 1, further comprising using the biometric values for a curvature of a rear of the cornea for the ray tracing method.

\* \* \* \* \*

UNITED STATES PATENT AND TRADEMARK OFFICE
CERTIFICATE OF CORRECTION

PATENT NO. : 10,194,797 B2
APPLICATION NO. : 15/167688
DATED : February 5, 2019
INVENTOR(S) : Rudolf Murai von Bünau et al.

Page 1 of 1

It is certified that error appears in the above-identified patent and that said Letters Patent is hereby corrected as shown below:

In the Claims

Column 8, Line 16, delete "tonic" and insert --toric--

Column 8, Line 17, delete "IDLs" and insert --IOLs--

Signed and Sealed this
Thirtieth Day of April, 2019

Andrei Iancu
*Director of the United States Patent and Trademark Office*